United States Patent
Aussant et al.

(10) Patent No.: US 11,060,050 B2
(45) Date of Patent: Jul. 13, 2021

(54) ORGANIC COMPOUNDS

(71) Applicant: GIVAUDAN SA, Vernier (CH)

(72) Inventors: Emmanuel Aussant, Paris (FR); Sandra Guinebretiere, Franconville (FR)

(73) Assignee: GIVAUDAN SA, Vernier (CH)

(*) Notice: Subject to any disclaimer, the term of this patent is extended or adjusted under 35 U.S.C. 154(b) by 0 days.

(21) Appl. No.: 16/603,051

(22) PCT Filed: Apr. 17, 2018

(86) PCT No.: PCT/EP2018/059764
§ 371 (c)(1),
(2) Date: Oct. 4, 2019

(87) PCT Pub. No.: WO2018/197266
PCT Pub. Date: Nov. 1, 2018

(65) Prior Publication Data
US 2020/0190441 A1    Jun. 18, 2020

(30) Foreign Application Priority Data
Apr. 28, 2017    (GB) .................................... 1706762

(51) Int. Cl.
*C11D 3/50* (2006.01)
*B01J 13/14* (2006.01)
*C11D 17/00* (2006.01)
*C11D 17/04* (2006.01)

(52) U.S. Cl.
CPC ............. *C11D 3/505* (2013.01); *B01J 13/14* (2013.01); *C11D 17/0004* (2013.01); *C11D 17/043* (2013.01)

(58) Field of Classification Search
CPC ..... C11D 3/505; C11D 17/0039; C11D 3/3796; C11D 17/0013; C11D 3/3769
See application file for complete search history.

(56) References Cited

U.S. PATENT DOCUMENTS

| | | | |
|---|---|---|---|
| 5,458,810 A | 10/1995 | Fredj et al. | |
| 5,460,752 A | 10/1995 | Fredj et al. | |
| 5,466,802 A | 11/1995 | Panandiker et al. | |
| 5,470,507 A | 11/1995 | Fredj et al. | |
| 5,731,278 A | 3/1998 | Nair et al. | |
| 5,916,862 A | 6/1999 | Morelli et al. | |
| 5,929,022 A | 7/1999 | Velazquez | |
| 6,815,410 B2 | 11/2004 | Boutique et al. | |
| 2018/0169603 A1* | 6/2018 | Harrison | C08G 12/32 |
| 2018/0193812 A1* | 7/2018 | Blondel | C11D 3/3796 |

FOREIGN PATENT DOCUMENTS

| | | |
|---|---|---|
| WO | 2004016234 A1 | 2/2004 |
| WO | 2006018694 A1 | 2/2006 |
| WO | 2016207180 A1 | 12/2016 |
| WO | 2016207187 A1 | 12/2016 |

OTHER PUBLICATIONS

International Search Report and Written Opinion of the International Searching Authority for corresponding application PCT/EP2018/059764 dated Jun. 5, 2018.
GB Search Report for corresponding application GB 1706762.0 dated Sep. 20, 2017.

* cited by examiner

*Primary Examiner* — John R Hardee
(74) *Attorney, Agent, or Firm* — Norris McLaughlin PA

(57) ABSTRACT

The invention relates to stable dispersion of negatively-charged aminoplast microcapsules in non-suspending detergent compositions containing an anionic surfactant. The microcapsules are stably dispersed by means of a cationic polyampholyte, which is embedded in the shells of said microcapsules.

20 Claims, No Drawings

ORGANIC COMPOUNDS

This is an application filed under 35 USC 371 based on PCT/EP2018/059764 (WO 2018/197266) filed 17 Apr. 2018, which in turn is based on GB 1706762.0 filed 28 Apr. 2017. The present application claims the full priority benefit of these prior applications and herein incorporates by reference the full disclosures of these prior applications.

FIELD

The present invention relates to dispersions of core-shell microcapsules, and in particular to the stabilization of said dispersions in the presence of anionic surfactants.

BACKGROUND OF THE INVENTION

It is known to incorporate encapsulated perfumes in consumer products, such as household care, personal care, and fabric care products. Perfumes are encapsulated for a variety of reasons. Microcapsules can isolate and protect perfume ingredients from external suspending media, such as consumer product bases, in which they may be incompatible or unstable. They are also used to assist in the deposition of perfume ingredients onto substrates, such as skin, hair, fabrics or hard household surfaces. They can also act as a means of controlling the spatio-temporal release of perfume.

Thermosetting resins are common encapsulating media for perfume compositions. Core-shell microcapsules formed from aminoplast resin, polyurea resin, polyurethane resin and combinations thereof are generally quite resistant to leakage when dispersed in aqueous suspending media, even in surfactant-containing aqueous suspending media. Furthermore, when incorporated into consumer products, such as laundry detergents or conditioners, they provide perfumery benefits that are unattainable from perfume incorporated directly into those products.

Particularly in relation to transparent or translucent consumer products, such as certain liquid detergents or shampoos, a principal requirement for the use of microcapsules is that they should disperse well into the product and not form aggregates that are visible to the eye.

A common way to avoid aggregation of microcapsules is to use a suspending agent, as the Brownian motion of microcapsules is hampered and the probability of two microcapsules to meet and aggregate is drastically reduced in suspending media.

However, non-suspending liquid detergents, such as the well-known liquid detergent unit dose product formats, sometimes referred to as "pouches" or "liquid-tabs", are especially prone to such phase separation phenomena, and those that are transparent or translucent are particularly problematic products, in which to incorporate encapsulated perfume compositions. Microcapsule aggregation may occur in these products upon storage. This lowers the performance of the product, causes problems in handling and/or makes the visual appearance of the product unattractive to consumers, providing a visual cue suggesting its deterioration.

There remains a need to provide methods and compositions for incorporating encapsulated perfumes into non-suspending liquid detergents, and particularly those liquid detergents that are intended to be employed as the fill in a unit dose pouch format.

Applicant surprisingly found a novel core-shell microcapsule composition that can be incorporated into non-suspending liquid detergent bases, substantially without the formation of visible aggregates, the aggregation-stability of the core-shell microcapsule composition being improved by means of a cationic polyampholyte being embedded within the microcapsule shell.

SUMMARY OF THE INVENTION

The invention provides in a first aspect an encapsulated perfume composition comprising at least one negatively-charged aminoplast core-shell microcapsule dispersed in an aqueous dispersion medium, the shell of the core-shell microcapsule having embedded therein a cationic polyampholyte.

The invention further provides the encapsulated perfume composition described above, wherein the at least one dispersed microcapsule has a zeta potential of about $-25$ mV or lower, for example between $-25$ mV and $-80$ mV; more particularly between $-35$ mV and $-60$ mV.

In a further aspect, the invention provides a non-suspending liquid detergent product containing an anionic surfactant, comprising the encapsulated perfume composition herein defined and an anionic surfactant.

In another aspect, there is provided the liquid detergent product described above enclosed within a water-soluble or water-dispersible film.

In another aspect, there is provided a method of reducing or eliminating the aggregation of aminoplast core-shell microcapsules in a non-suspending liquid detergent product containing an anionic surfactant, and in particular a liquid detergent product in single dose or pouched format, the method comprising the step of embedding a cationic polyampholyte in the shells of the core-shell microcapsules.

In a further aspect, the invention provides a method of forming an encapsulated perfume composition as defined above, the method comprising the steps of:
 i) forming a slurry comprising at least one aminoplast core-shell microcapsule dispersed in an aqueous dispersing medium; and
 ii) adding to the slurry a cationic polyampholyte, an amino-aldehyde pre-condensate and a cross-linker, under conditions to form a cross-linked matrix of aminoplast resin around said at least one aminoplast core-shell microcapsule, wherein the cationic polyampholyte is embedded in said matrix.

These and other aspects and embodiments of the invention will be further described with reference to the following detailed description of the invention.

DETAILED DESCRIPTION OF THE INVENTION

Conventional aminoplast core-shell microcapsules, such as melamine-formaldehyde microcapsules, are negatively charged. A dispersion of such microcapsules in a potassium dihydrogen phosphate/sodium hydrogen phosphate buffer solution at pH 7, having an ion concentration of $7 \times 10^{-4}$ mol/l, typically has a zeta potential of about $-35$ mV to $-80$ mV, more particularly from $-40$ mV to $-70$ mV, more particularly from $-50$ mV to $-60$ mV.

It is known that such microcapsules can be incorporated into surfactant-containing media, such as fabric conditioner compositions, without any visible signs of aggregation.

The applicant was therefore surprised to observe that dispersions of negatively-charged aminoplast core-shell microcapsules displayed an alarming tendency to undergo visible signs of aggregation when incorporated into non-suspending detergent bases predominantly comprising anionic surfactants. The applicant found that this was particularly apparent in those detergent bases commonly employed in unit dose, pouched formats: This tendency was particularly apparent in those water-clear, transparent or slightly hazy non-suspending bases typically used in these formats. This observation is surprising because the skilled formulator would expect that negatively-charged core-shell microcapsules and anionic surfactants would be fully compatible and that negatively-charged microcapsules would disperse easily in such anionic surfactant-rich media.

The applicant has now found that such unexpected aggregation phenomena can be reduced or eliminated by embedding cationic polyampholytes in the shells of such negatively-charged core-shell microcapsules. In particular, using the cationic polyampholytes, aggregation phenomena, such as flocculation or agglomeration, of core-shell microcapsules during storage of anionic surfactant-containing non-suspending detergent products containing same is suppressed. Furthermore, the olfactive performance of encapsulated perfume compositions containing the modified core-shell microcapsules is not adversely affected, or may even be improved by the incorporation of the cationic polyampholyte within the shells. The observation that an embedded cationic polyampholyte can increase the compatibility of a dispersion of negatively-charged core-shell microcapsules in such anionic surfactant-containing media is especially surprising and counter-intuitive to anybody skilled in the art.

As used herein, the term "embedded" or "embedding" as it relates to the cationic polyampholyte means that the polyampholyte is, at least partially, physically entrapped in a matrix of cross-linked aminoplast resin that is formed around an already formed core-shell microcapsule.

The applicant surprisingly found that embedded cationic polyampholyte was effective in preventing the aggregation of aminoplast core-shell microcapsules in the aforementioned detergent bases.

Furthermore, the conventional treatment of an aminoplast core-shell microcapsule slurry with a solution of cationic deposition aid is not effective in ameliorating the observed aggregation phenomenon.

The level of embedded cationic polyampholyte employed in the formation of core-shell microcapsules in order to reduce or eliminate visible signs of aggregation are not particularly important, and may range from 0.01 to 5 wt %, based on the total weight of the slurry (i.e. the weight of microcapsules and dispersing medium). However, in order to reduce any possible negative impact on the performance of the microcapsules, such as leakage stability, it is preferred to use as low levels of cationic polyampholyte as possible, and the applicant found that aggregation phenomena can be eliminated or effectively reduced even when employing levels of cationic polyampholyte as low as about 0.5 wt %.

The term "non-suspending" as used herein in relation to a detergent base refers to a detergent base that does not show any viscosity peak and/or any significant viscosity drop, for example by more than 5 Pa·s, or by more than 10 Pa·s, when submitted to increasing shear rate from 0.01 to 0.1 $s^{-1}$, and wherein the value of the viscosity in this range of shear rates is lower than 10 Pa·s, more particularly lower than 5 Pa·s at 25° C., as measured on a standard rheometer apparatus, for example a Thermo Haake Rheostress 1 (equipped with a RheoWin 4.20.0004 software, equipped with a thermostated plate-plate P60 Ti L measuring cell).

The terms "flocculation" and "agglomeration" used hereinabove are art recognized terms. Agglomeration refers to a phenomenon whereby microcapsules form loose, reversible aggregates that can be re-dispersed by applying a physical action, such as shaking or mixing. Flocculation, on the other hand, refers to the formation of aggregates that cannot be re-dispersed by applying a physical action, such as shaking or mixing.

As stated herein above, the present invention is concerned with means for the stable dispersion of negatively-charged aminoplast core-shell microcapsules into certain detergent bases containing anionic surfactants, such as those used in unit dose, pouched format, the means being provided by the embedding of a cationic polyampholyte into the shells of the core-shell microcapsules.

Within the terms of the present invention, a negatively-charged aminoplast microcapsule is such a microcapsule bearing a net negative charge, which can be quantified by measuring its zeta potential in a manner known per se. The zeta potential of the core-shell microcapsules of the present invention in the buffered solution is typically at least about −25 mV, and more particularly at least about −30 mV, and more particularly at least about −35 mV.

As is well known to the person skilled in the art, "zeta-potential" (ζ) is a measure of the apparent electrostatic potential generated by any electrically charged objects in a solution or a suspension, as measured by specific measurement techniques. A detailed discussion of the theoretical basis and practical relevance of the zeta-potential can be found, e.g., in "Zeta Potential in Colloid Sciences" (Robert. J. Hunter; Academic Press, London 1981, 1988). The zeta-potential of an object is measured at some distance from the surface of the object and is generally not equal to and lower than the electrostatic potential at the surface itself. Nevertheless, its value provides a suitable measure of the capability of the object to establish electrostatic interactions with other objects present in the dispersion, such as surfactants, polyelectrolytes and surfaces. In the present case, the zeta-potential of the core-shell microcapsules is measured by laser diffraction. A suitable instrument for measuring the parameter is a Zetasizer Nano Z available from Malvern Instruments SARL equipped with a Malvern Capillary Cell DTS 10.70. Before measurement, a microcapsule suspension was treated as follows: A microcapsule dispersion formed according to a method of the present invention was filtered, and the microcapsules were washed 5 times with distilled water and re-dispersed again in distilled water. 2 g of this dispersion was added to 8 g of a potassium dihydrogen phosphate/sodium hydrogen phosphate buffer solution at pH 7, corresponding to an ion concentration of $7.10^{-4}$ mol/l. A laser with a wavelength of 633 nm was used for the measurements.

A cationic polyampholyte useful in the present invention is a co-polymer bearing cationic functional groups or bearing functional groups capable of forming cations under the conditions in which it is employed in the present invention. The cationic polyampholyte may also contain anionic functional groups, or functional groups that may form anions under the conditions in which it is employed in the present invention, provided that the cationic polyampholyte possesses a net positive charge under the conditions in which it is employed in the present invention.

In one embodiment, the cationic polyampholyte according to the invention is an amphoteric co-polymer, which bears one or more of cationic functional groups, and/or functional groups that can form cations under the conditions in which it is employed in the present invention; and anionic functional groups, and/or functional groups that can form anions under the conditions in which it is employed in the present invention. The cationic polyampholyte may also contain non-ionic functional groups.

The functional groups are present on the monomers from which the co-polymer is formed, and, if not inherently anionic or cationic, can be modified to be so, subsequent to polymerization. Thus, a cationic functional group is derived from a cationic monomer; a cation-forming functional group is derived from a monomer containing a functional group that can be present in cationic form; an anion-forming functional group is derived from a monomer containing a functional group that can be present in anionic form; and a non-ionic functional group is derived from a non-ionic monomer.

In one embodiment, monomers bearing cationic functional groups may be selected from the group consisting of quaternized nitrogen functionality, such as quaternized primary, secondary and tertiary alkyl and allyl amines, quaternized pyridine, quaternized imidazole, quaternized pyrrolidine, or quaternized phosphorous, trisubstituted sulfur, and the like. In particular, such cationic monomers are preferably selected from the group consisting of quaternized dimethylaminoethyl acrylate (ADAME), quaternized dimethylaminoethyl methacrylate (MADAME), diallyidimethylammonium chloride, dimethyldiallyl ammonium chloride (DADMAC), acrylamidopropyltrimethylammonium chloride (APTAC), methacrylamidopropyltrimethylammonium chloride (MAPTAC), methacryloylaminopropyl lauryl-dimonium chloride, and quaternized vinyl pyridine.

In a preferred embodiment, the cationic monomers are selected from DADMAC and MAPTAC.

In one embodiment, the cation-forming functional groups are capable of forming cations under defined pH conditions.

In one embodiment, the cation-forming functional groups can form cations at a pH of 8 or lower, 7 or lower, 5 or lower. Suitable cation-forming functional groups include but are not limited to vinyl, allyl, acrylic and methacrylic monomers bearing protonizable amines, such as primary, secondary amines and amine oxides; N,N-dimethylaminoalkyl methacrylate, vinyl pyridine, vinyl amine, allyl amine, vinyl imidazoline, vinyl imidazole, amino-functionalized alkoxysilane, and polyethylenimine macromers.

In one embodiment, the anion-forming functional groups are capable of forming anions under defined pH conditions.

In an embodiment, the anion-forming functional groups can form anions at a pH of 4 and higher, e.g. 5 or higher, or 6 or higher, or 7 or higher. Functional groups that can form anions may be derived from monomers selected from the group consisting of acrylic based monomers, including acrylic acid, methacrylic acid, itaconic acid, crotonic acid, maleic acid, and fumaric acid. The acrylic-based monomer may also be any water-soluble salt of these monomers; wherein the salt is preferably a salt of an alkali metal, an alkaline-earth metal or an ammonium salt.

Strong-acid monomers that can form anions at lower pH, for example at a pH of 3 and higher, 2 and higher, or 1 and higher, such as for example monomers with a sulfonic acid or a phosphonic acid-type function such as 2-acrylamido-2-methylpropane sulfonic acid, vinylsulfonic acid, vinylphosphonic acid, allylsulfonic acid, allylphosphonic acid, styrene sulfonic acid, may also be used.

In a preferred embodiment, the anionic monomer is acrylic acid or methacrylic acid.

A non-ionic functional group may be derived from a non-ionic monomer selected from the group consisting of water-soluble vinyl monomers, and more particularly acrylamide, methacrylamide, N-isopropylacrylamide, N,N-dimethylacrylamide, N-methylolacryl-amide, N-vinylformamide, N-vinyl acetamide, N-vinylpyridine and N-vinylpyrrolidone.

In a preferred embodiment, the non-ionic monomer is acrylamide.

In an embodiment of the invention, the cationic polyampholyte comprises 1 to 99 mol % of a cationic or a cation-forming functional group; and 1 to 99 mol % of an anion-forming functional group.

In a more particular embodiment, the cationic polyampholyte may be a terpolymer comprising 1 to 99 mol % of a cationic functional group or a cation-forming functional group; 1 to 99 mol % of an anion-forming functional group and 0 to 50 mol % of a non-ionic functional group.

In an embodiment of the invention, the cationic polyampholyte comprises 2 to 99 mol % still more particularly 30 to 95 mol %, and more particularly still 60 to 90 mol % of a cationic functional group or cation-forming functional group and 1 to 98 mol %, more particularly 5 to 70 mol %, still more particularly 10 to 40 mol % of an anion-forming functional group; and 0 to 50 mol %, and more particularly 0.1 to 5 mol % of a non-ionic functional group.

In an embodiment of the invention, the cationic functional groups are pH independent.

In an embodiment of the invention, the cationic functional groups are quaternary ammonium groups.

In a particular embodiment, the cationic polyampholyte is formed from a cationic monomer containing quaternary ammonium groups and a monomer that can form anion-forming functional groups, more particularly a monomer that is based on acrylic acid, methacrylic acid or a derivative thereof.

In a more particular embodiment, the cationic polyampholyte is a co-polymer of acrylic acid or methacrylic acid and dimethyldiallyl ammonium chloride (DADMAC), such as polyquaternium-22 (CAS Registry Number 53694-17-0), or a co-polymer of acrylic acid or methacrylic acid and methacrylamidopropyl-trimethylammonium chloride (MAPTAC).

In a still more particular embodiment, the cationic polyampholyte is a terpolymer formed from acrylic acid monomer, DADMAC, polyquaternium-39 (CAS Registry Number 25136-75-8) or MAPTAC monomer and acrylamide monomer, such as polyquartenium-53 (CAS Registry Number 53 84647-38-1).

In an embodiment, the acrylic acid/DADMAC co-polymer, and more particularly the terpolymer, is formed by reacting 1 molar equivalent of acrylic acid monomer with 1 to 4 molar equivalents of the DADMAC monomer (for example Merquat 281), more particularly 1 molar equivalent of acrylic acid monomer with 1 to 2.5 molar equivalents of DADMAC monomer, and still more particularly 1 molar equivalents of acrylic acid monomer with 1 to 2 molar equivalents of DADMAC monomer.

In an embodiment, the acrylic acid/MAPTAC co-polymer, and more particularly the terpolymer, is formed by reacting 1 to 2 molar equivalents of acrylic acid monomer with 4 molar equivalents of the MAPTAC monomer, more particularly 1 molar equivalent of acrylic acid monomer to 4 molar equivalents of MAPTAC monomer and still more particularly 1.6 molar equivalents of acrylic acid monomer to 4 molar equivalents of MAPTAC monomer.

In an embodiment of the invention, the co-polymer has a molecular weight of at least 100'000 g/mol, and more particularly at least 500'000 g/mol.

The cationic polyampholyte can be prepared using polymerization techniques that are well known to a person skilled in the art. These known polymerization techniques include solution polymerization; gel polymerization; precipitation polymerization; inverse emulsion polymerization; aqueous emulsion polymerization; suspension polymerization; and micellar polymerization.

The cationic polyampholyte can be cross-linked by at least one cross-linking agent, which may be chosen from the group consisting of polyethylenically unsaturated monomers (having at least two unsaturated functional groups such as for example vinyl, allyl, and acrylic), and compounds having epoxy functional groups. For instance, such cross-linking agents include methylene bisacrylamide (MBA), triallyamine and polyethylene glycol diacrylate. Alternatively, macro initiators such as polyperoxides, polyazo compounds and polytransfer agents such as polymercaptan polymers may be used.

The cationic polyampholyte may be a cross-polymer.

As stated hereinabove, the encapsulated perfume compositions of the present invention can be incorporated into certain liquid detergent bases containing anionic surfactants without the appearance of the visible signs of aggregation of the core-shell microcapsules.

The encapsulated perfume composition described above is intended to be dispersed in a non-suspending detergent base.

The non-suspending detergent base may be a concentrated detergent base and especially a concentrated detergent base typically employed in unit dose, pouched format as described hereunder in more detail. The detergent may be a transparent, hazy or water-clear liquid detergent. However, opaque or translucent non-suspending bases may also be used.

In another embodiment, the slurry may be dispersed in a detergent base that is a shampoo, a shower gel, a liquid soap or an extruded product, such as an extruded soap product.

Examples of suitable detergent bases are to be found in: Formulating Detergents and Personal Care Products: A guide to Product Development, by L Ho Tan Tai, ISBN 1-893997-10-3 published by the AOCS Press. Also to Volume 67 of the Surfactant Science Series Liquid Detergents ISBN 0-8247-9391-9 (Marcel Dekker Inc), as well as in the patent literature, for example the following U.S. Pat. Nos. 5,929,022; 5,916,862; 5,731,278; 5,470,507; 5,466,802; 5,460,752; and 5,458,810.

Detergent bases in which the encapsulated perfume composition of the present invention is to be dispersed comprise anionic, and optionally non-ionic surfactants, and mixtures thereof.

Typical anionic surfactants include sodium lauryl sulfate, sodium laureth sulfate, sodium trideceth sulfate, ammonium lauryl sulfate, ammonium laureth sulfate, potassium laureth sulfate, linear alkyl benzene sulfonates, sodium tridecyl benzene sulfonate, sodium dodecyl benzene sulfonate, sodium xylene sulfonate, monoethanolamine lauryl sulfate, monoethanolamine laureth sulfate, triethanolamine lauryl sulfate, triethanolamine laureth sulfate, lauryl sarcosine, cocoyl sarcosine, sodium lauryl sarcosinate, sodium lauroyl sarcosinate, triethylamine lauryl sulfate, triethylamine laureth sulfate, diethanolamine lauryl sulfate, diethanolamine laureth sulfate, lauric monoglyceride sodium sulfate, ammonium cocoyl sulfate, ammonium lauroyl sulfate, sodium cocoyl sulfate, sodium lauroyl sulfate, sodium cocoyl isethionate, potassium cocoyl sulfate, potassium lauryl sulfate, monoethanolamine cocoyl sulfate, monoethanolamine lauryl sulfate, triethanolamine lauryl sulfate, C5-C17 acyl-N—(C1-C4 alkyl) glucamine sulfate, C5-C17 acyl-N—(C1-C4 hydroxyalkyl) glucamine sulfate, sodium hydroxyethyl-2-decyl ether sulfates, sodium methyl-2-hydroxydecyl ether sulfates, sodium hydroxyethyl-2-dodecyl ether sulfates, sodium monoethoxylated lauryl alkyl sulfates, C12-C18 alkyl sulfonates, ethoxylated or native linear and ramified C12-C18 alcohol sulfates, ethoxylated or native linear and ramified C12-C18 alcohol sulfates, and mixtures thereof. The above-mentioned anionic surfactants may also be used in their un-neutralized, acid form. The level of anionic surfactants in liquid detergents that may be considered as suitable dispersion media for the core-shell microcapsules according to the present invention is from about 1 wt % to about 40 wt %, more particularly from about 5 wt % to about 35 wt %.

In non-suspending detergent bases, especially relevant in the context of the present invention, the level of anionic surfactants is typically from about 5 wt % to about 15 wt %.

Typical non-ionic surfactants include C6-C24 alkyl ethoxylates with about 1-12 ethylene oxide units. The alkyl chain of the aliphatic alcohol can either be straight or branched, primary or secondary, and generally contains from about 6 to about 22 carbon atoms. Further examples of non-ionic surfactants include the condensation products of fatty acids with glucamines, such as C12-C16 akyl N-methyl glucamide, and/or the condensation product of fatty acids with ethoxylated amines; C10-C20 alkyl mono- or di-alkanolamides, where the alkyloxy group has 1 to 3 carbon atoms, C10-C20 alkyl mono- or di-alknolamide having an intermediate polyoxyalkylene moiety having 2 to 20 alkyleneoxide groups between the alkyl moiety and the alkanolamide moiety; alkyl amidopropyl dimethylamine; fatty acid alkyl esters, such as sorbitol esters with oleic, myristic, stearic, palmitic acid, and the like, also known under the trade name Tween, such as Tween 20, Tween 40, and Tween 60; alkyl polyglycosides including, for example, C8-C10 alkyl polyglycosides, C12-C16 alkyl polyglycosides, C5 Amyl. Further non-ionic surfactants include glycerol-based surfactants, such as fatty acid polyglyceryl esters like octanoic acid hexaglyceryl ester, decanoic acid tetraglyceryl ester, riccinoleic acid hexaglyceryl ester and cocoic acids tetraglyceryl esters and their mixtures. The term "alkyl" as used hereinabove for the non-ionic sugar-based surfactant refers to saturated linear alkyl residues having 3 to 21 carbon atoms, including hexyl, octyl, decanyl, dodecanyl, tetradecanyl, hexadecanyl, and octadecanyl.

The level of non-ionic surfactants employed in detergent bases is from about 0 wt % to about 40 wt %, more particularly from about 10 wt % to about 35 wt %, with respect to the total weight of the detergent base.

In some cases, the detergent base may also comprise cationic, cationogenic, zwitterionic and/or amphoteric detergents.

The incorporation of encapsulated perfume compositions described herein into detergents for use in unit dose, pouched format represents a particular embodiment of the present invention.

Unit dose, pouched formats are well known in the art (see for example U.S. Pat. No. 6,815,410). Pouched formats typically comprise a liquid detergent base surrounded by a water-soluble or water-dispersible film. Owing to the fact that these liquid detergent compositions are contained within water-soluble or dispersible film, they are characterized by high levels of surfactants and very low concentrations of water. The applicant observed that the aggregation phenomenon was particularly evident with conventional aminoplast core-shell microcapsules.

Preferred water-soluble or water-dispersible films are comprised of polymers and co-polymers based on polyvinylalcohol, and thermoplastic starch derivatives, wherein polyvinylalcohol-based polymers are the most often used. Liquid detergent composition that can be held in water-soluble pouches may typically comprise water, solvents, bleaching agents, enzymes, enzyme stabilizing systems, chelating agents, surfactants, neutralizing agents, builders, fillers, anti-redeposition or soil dispersing polymers, fabric caring or enhancing polymers, dye transfer inhibitors, flocculating, deflocculating and thickening agents, fabric softening agents; and mixture thereof. Such compositions contain preferably less than 0.2% of borate ions, but are preferably essentially free of borate or perborate.

The detergent base may also contain solids and gases, either in the dissolved form or in the form of particle (for solids) or bubbles (for gases).

The level of water in the detergent base used in a unit dose, pouched format is such that the water-soluble or water-dispersible polymer forming the pouch does not dissolve or disperse as a result of contact with the detergent base. The level of water in the detergent base is less than 50% by weight, more particularly less than 20% by weight, still more particularly less than 10% by weight, and may be even as low as about 5% by weight of the detergent base.

Neutralizing agents that may be employed in a detergent base are preferably selected from basic organic compounds such as amines, e.g. mono-ethanolamine, triethanolamine, organic Lewis bases, and mixtures thereof, but inorganic bases, such as sodium hydroxide, potassium hydroxide and ammonium hydroxide, can also be used. The level of neutralizing agent in the detergent is typically from 5 to 15% by weight of the detergent, although lower or higher levels can also be used.

Preferred solvents are those solvents which do not dissolve or disperse the polymer used to form the pouch. These solvents may have a low polarity or a high polarity. Low polarity solvents include typically linear and/or branched paraffin hydrocarbons. High polarity, water-soluble or partially soluble, or water miscible solvents include typically alcohols, such as methanol, ethanol, propanol, isopropanol, butanol; diols, such as 1,2-propanediol, 1,3-propanediol, glycerol, sorbitol, 2-amino-2-ethyl propanol, ethers, polyethers, short chain di-, tri-N-substituted alkylamines, short chain alkyl amides, short chain alkyl carboxylic acid lower alkyl esters, ketones, such as short chain alkyl ketones, including acetone. The liquid composition may comprise from 10% to 70% by weight of water-soluble solvents having molecular weight higher than 70 g/mol.

A typical liquid detergent base for use in pouches may, for example, contain 10 wt % of deionized water, 20 wt % of propylene glycol, 18.5 wt % of glycerol, 16.47 wt % of sodium lauryl ether sulfate (for example TEXAPON® N 70, ex COGNIS), 5 wt % of benzenesulfonic acid, 5 wt % lauryl acid, 10 wt % monoethanolamine, 15 wt % of C12-C15 ethoxylated alcohols (for example NEODOL® 25-7, ex CALDIC) and 0.03 wt % preservative (for example 2-bromo-2-nitropropane, available under the trade name BRONIDOX®, ex COGNIS).

The levels at which the encapsulated perfume composition may be incorporated into a detergent composition is conventional, and may vary depending upon the particular detergent base in which the encapsulated perfume composition is being incorporated. For example, the encapsulated perfume composition may be employed in amounts of about 0.005 wt % to about 50 wt %, still more particularly about 0.01 wt % to about 20 wt %, and more particularly still about 0.1 wt % to about 5 wt %, based on the total weight of the composition.

Core-shell microcapsules of the encapsulated perfume composition can be formed by the poly-condensation reaction of conventional shell-forming materials. Suitable shell-forming materials are well known in the art. Particularly useful shell-forming materials are any of the amino-aldehyde pre-condensates known in the art. The amino-aldehyde pre-condensate may be a reaction product, such as a polymer or co-polymer of at least one amine, such as urea, thiourea, alkyl urea, 6-substituted-2,4-diamino-1,3,5-triazines such as benzoguanamine or glycoluril, and melamine; and at least one aldehyde, such as formaldehyde, acetaldehyde, glyoxal or glutaraldehyde. Suitable amino-aldehyde pre-condensates include but are not limited to partially methylated mono- and poly-methylol-1,3,5-triamino-2,4,6-triazine pre-condensates, such as those commercially available under the Trade Mark CYMEL (ex Cytec Technology Corp.) or LURACOLL (ex BASF), and/or mono- and polyalkylol-benzoguanamine pre-condensates, and/or mono- and polyalkylol-glycouril pre-condensates. These alkylolated polyamines may be provided in partially alkylated forms, obtained by addition of short chain alcohols having typically 1 to 6 methylene units.

During microcapsule formation it is conventional to employ a colloid stabilizer to stabilize the oil-water interface during microcapsule formation. The stabilizer functions in several ways: It ensures that stable oil-in-water emulsions are formed allowing migration of shell-forming materials, e.g. the pre-condensate and cross-linker to the oil-water interface; and it functions essentially as a template around which poly-condensation and cross-linking reactions can take place to form the encapsulating cross-linked aminoplast resin shells. Colloid stabilizers can also prevent the formed microcapsules from agglomerating.

Some of the colloid stabilizer will be washed out of the microcapsules as they form, but some will be retained within the encapsulating shells and become part of the shells. Particular examples of suitable colloid stabilizers include acrylic copolymers bearing sulfonate groups, such as those available commercially under the trade mark LUPASOL (ex BASF), such as LUPASOL PA 140 or LUPASOL VFR; copolymers of acrylamide and acrylic acid, copolymers of alkyl acrylates and N-vinylpyrrolidone, such as those available under the trade mark Luviskol (e.g. LUVISKOL K 15, K 30 or K 90 ex BASF); sodium polycarboxylates (ex Polyscience Inc.) or sodium poly(styrene sulfonate) (ex Polyscience Inc.); vinyl and methyl vinyl ether-maleic anhydride copolymers (e.g. AGRIMER™ VEMA™ AN, ex ISP), and ethylene, isobutylene or styrenemaleic anhydride copolymers (e.g. ZEMAC™). Hence the preferred stabilizers are anionic polyelectrolytes.

In a preferred embodiment, a melamine-formaldehyde pre-condensate is used in the formation of the core-shell microcapsules. The melamine-formaldehyde pre-condensate is formed by the reaction of melamine with formaldehyde to form methylolated melamine. Methylolated melamine may also be treated with methanol to form methoxymethylated methylol melamine, which may also be employed as a pre-condensate in a process of core-shell microcapsule formation.

In a preferred embodiment, a diamine cross-linker is used to cross-link the melamine-formaldehyde pre-condensate during core-shell microcapsule formation. Particular examples of diamines useful in the present invention include, but are not limited to, urea, benzoguanamine, benzoguanidine, poly[N-(2,2-dimethoxy-1-hydroxy)] polyamines, including di-[N-(2,2-dimethoxy-1-hydroxy)]

urea, di-[N-(2,2-dimethoxy-1-hydroxy)] benzoguanamine and di-[N-(2,2-dimethoxy-1-hydroxy)] benzoguanidin.

A particularly suitable diamine cross-linker is urea.

The cationic polyampholyte is embedded in the shells of the core-shell microcapsules during the process of microcapsule formation.

More particularly, the cationic polyampholyte is embedded in at least one layer of cross-linked aminoplast resin deposited on a pre-formed aminoplast core-shell microcapsule.

More particularly still, the shell of the core-shell microcapsule is built-up in a sequential series of steps, whereby in a first step a first part of the shell-forming material comprising amino-aldehyde pre-condensate and cross-linker is poly-condensed around droplets of core material to form a slurry of core-shell microcapsules dispersed in an aqueous dispersion medium; and in a subsequent step the cationic polyampholyte and a subsequent part of the shell-forming material comprising amino-aldehyde pre-condensate and cross-linker material are added to the slurry, and poly-condensed around the core-shell microcapsules to form a cross-linked matrix of melamine-formaldehyde resin around said core-shell microcapsules, wherein the cationic polyampholyte is embedded in said matrix.

In a more particular embodiment, in said subsequent step, the cationic polyampholyte and the subsequent part of the shell-forming material may be added to the slurry of core-shell microcapsules simultaneously or sequentially, provided that the cationic polyampholyte is in admixture with the subsequent part of the shell-forming material before it is poly-condensed around the core-shell microcapsules.

Accordingly, in a particular embodiment of the present invention, there is provided a method of forming an encapsulated perfume composition comprising at least one aminoplast core-shell microcapsule dispersed in a dispersing medium, said method comprising the steps of:

I) encapsulating at least on perfume-containing droplet in a shell comprising a cross-linked aminoplast, resin to form a slurry comprising a dispersion of at least one aminoplast core-shell microcapsule; and II) adding to the slurry, simultaneously or sequentially, the cationic polyampholyte, an amino-aldehyde pre-condensate, and a cross-linker, under conditions whereby the pre-condensate and cross-linker react to form a matrix cross-linked aminoplast resin around the core-shell microcapsule, in which matrix the cationic polyampholyte is embedded.

In a more particular embodiment of the present invention, there is provided a method of forming an encapsulated perfume composition comprising at least one aminoplast core-shell microcapsule dispersed in a dispersing medium, said method comprising the steps of:

I) mixing together, at a temperature of about 35° C. and a pH of about 4.5, a polymeric stabilizer, perfume-containing oil, amino-aldehyde pre-condensate (e.g. melamine-formaldehyde pre-condensate), and a cross-linker (e.g. diamine cross-linker), in water and under moderate shear;

II) emulsifying the mixture to obtain a desired average droplet size range and droplet size distribution;

III) raising the temperature above about 80° C. over a period of about 3 h, to form a cross-linked aminoplast resin shell around the droplets, thereby forming a slurry of coreshell microcapsules;

IV) at a pH of about 4.5, adding sequentially or simultaneously the cationic polyampholyte, amino-aldehyde pre-condensate (e.g. melamine-formaldehyde pre-condensate) and a cross-linker (e.g. diamine cross-linker), and keeping the temperature above about 80° C. over a period of about 2 h, forming a matrix of cross-linked aminoplast resin around the core-shell microcapsules, in which matrix the cationic polyampholyte is embedded; and V) cooling the resultant slurry.

In forming the emulsion according to step II), the skilled person in the art can select an appropriate stirring speed and geometry of the mixer in order to obtain the desired average droplet size and droplet size distribution.

In carrying out step IV), it is preferred if the cationic polyampholyte is added to the slurry before the amino-aldehyde pre-condensate and cross-linker are added.

If desired, a formaldehyde scavenger may be added to the slurry of step V).

A formaldehyde scavenger may also be added to the slurry before the cooling step, in which case it is preferred if the formaldehyde scavenger is allowed to react for up to about 20 minutes before cooling. Typical formaldehyde scavengers comprise compounds capable of binding free formaldehyde in aqueous media, such as sodium sulfite, melamine, glycine, and carbohydrazine.

By means of the foregoing process, it is possible to incorporate an aggregate-stabilizing amount of cationic polyampholyte into aminoplast core-shell microcapsules. More particularly, it is possible to provide an aggregate-stabilizing effect using only about 0.2 wt % to about 1 wt % of cationic polyampholyte, based on the total weight of the core-shell microcapsule slurry.

The skilled person would appreciate the desirability of using only low levels of cationic polyampholyte because amino-aldehyde resins, and in particular melamine-formaldehyde resins, are particularly effective encapsulating media, and the incorporation of excessive amounts of foreign materials into the resin shells can affect the encapsulation efficiency of the microcapsules as well as their stability towards leakage of perfume from the encapsulated cores.

The slurry of core-shell microcapsules may contain more than 39 wt % of core-shell microcapsules dispersed in an aqueous phase, preferably more than 40 wt % and up to 42 wt % or more, based on the total weight of the slurry.

In one embodiment, the level of microcapsules in the slurry is 42 wt %, wherein this level is calculated based on the total amount of perfume-containing oil and shell-forming material employed in the microencapsulation process. Slurries containing less than about 39 wt % are less desirable for economic considerations, at least.

A suspending agent may be added to the slurry under stirring to insure that the microcapsules are stably suspended in the slurry and do not phase separate by creaming or sedimentation. Typically, hydrocolloids are used to improve the colloidal stability of the slurry against coagulation, sedimentation and creaming.

The term "hydrocolloid" refers to a broad class of water-soluble or water-dispersible polymers having anionic, cationic, zwitterionic or non-ionic character. Hydrocolloids useful for the sake of the present invention encompass: polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidoneco-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quartenized forms.

Preferably, Carbopol ETD 2561, a lightly crosslinked polyacrylic acid polymer, is used.

Preferably, the suspending agent is added to the slurry in a sufficient quantity to obtain a final viscosity in the range of 100 mPa·s to 3500 mPa·s, more preferably from 250 mPa·s to 2500 mPa·s at 25° C. and at a shear rate of 20 s$^{-1}$.

Although the core-shell microcapsules described hereinabove are employed to encapsulate perfume compositions, the skilled person will appreciate that other materials may form the core material. In fact, the core material may be any hydrophobic, water-insoluble or sparingly soluble material providing benefits, such as a functional benefit or a sensory benefit. For example, the core material may be an enzyme, a bleaching agent, a biocide, a whitener, a malodor counteracting agent, a cosmetic agent, and the like.

The cationic polyampholyte is used to stabilize the core-shell microcapsules when dispersed in an anionic surfactant-containing detergent base of the type described herein.

A comprehensive list of perfume ingredients that may be encapsulated in accordance with the present invention may be found in the perfumery literature, for example "Perfume & Flavor Chemicals", S. Arctander (Allured Publishing, 1994), as well as later editions of this work, which are herein incorporated by reference. Encapsulated perfume according to the present invention comprise preferably perfume ingredients selected from ADOXAL (2,6,10-trimethylundec-9-enal); AGRUMEX (2-(tert-butyl)cyclohexyl acetate); ALDEHYDE C 10 DECYLIC (decanal); ALDEHYDE C 11 MOA (2-methyldecanal); ALDEHYDE C 11 UNDECYLENIC (undec-10-enal); ALDEHYDE C 110 UNDECYLIC (undecanal); ALDEHYDE C 12 LAURIC (dodecanal); ALDEHYDE C 12 MNA PURE (2-methylundecanal); ALDEHYDE ISO C 11 ((E)-undec-9-enal); ALDEHYDE MANDARINE ((E)-dodec-2-enal); ALLYL AMYL GLYCOLATE (prop-2-enyl 2-(3-methylbutoxy)acetate); ALLYL CYCLOHEXYL PROPIONATE prop-2-enyl 3-cyclohexylpropanoate); ALLYL OENANTHATE (prop-2-enyl heptanoate); AMBER CORE (1-((2-(tert-butyl)cyclohexyl)oxy)butan-2-ol); AMBERMAX (1,3,4,5,6,7-hexahydro-.beta.,1,1,5,5-pentamethyl-2H-2,4a-methanonaphthalene-8-ethanol); AMYL SALICYLATE (pentyl 2-hydroxybenzoate); APHERMATE (1-(3,3-dimethylcyclohexyl)ethyl formate); BELAMBRE ((1R,2S,4R)-2$^{7}$-isopropyl-1,7,7-trim ethylspiro[bicyclo[2.2.1]heptane-2,4'-[1,3]dioxane]); BIGARYL (8-(sec-butyl)-5,6,7,8-tetra hydroquinoline); BOISAMBRENE FORTE ((ethoxymethoxy)cyclododecane); BOISIRIS ((1S,2R,5R)-2-ethoxy-2,6,6-trimethyl-9-methylenebicyclo[3.3.1]nonane); BORNYL ACETATE ((2S,4S)-1,7,7-trimethylbicyclo[2.2.1]heptan-2-yl acetate); BUTYL BUTYRO LACTATE (1-butoxy-1-oxopropan-2-yl butanoate); BUTYL CYCLOHEXYL ACETATE PARA (4-(tert-butyl) cyclohexyl acetate); CARYOPHYLLENE ((Z)-4,11,11-trimethyl-8-methylenebicyclo[7.2.0]undec-4-ene); CASHMERAN (1,1,2,3,3-pentamethyl-2,3,6,7-tetrahydro-1H-inden-4(5H)-one); CASSYRANE (5-tert-butyl-2-methyl-5-propyl-2H-furan); CITRAL ((E)-3,7-dimethylocta-2,6-dienal); CITRAL LEMAROME N ((E)-3,7-dimethylocta-2,6-dienal); CITRATHAL R ((Z)-1,1-diethoxy-3,7-dimethylocta-2,6-diene); CITRONELLAL (3,7-dimethyloct-6-enal); CITRONELLOL (3,7-dimethyloct-6-en-1-ol); CITRONELLYL ACETATE (3,7-dimethyloct-6-en-1-yl acetate); CITRONELLYL FORMATE (3,7-dimethyloct-6-en-1-yl formate); CITRONELLYL NITRILE (3,7-dimethyloct-6-enenitrile); CITRONELLYL PROPIONATE (3,7-dimethyloct-6-en-1-yl propionate); CLONAL (dodecanenitrile); CORANOL (4-cyclohexyl-2-methylbutan-2-ol); COSMONE ((Z)-3-methylcyclotetradec-5-enone); CYCLAMEN ALDEHYDE (3-(4-isopropyl phenyl)-2-methyl propana 1); CYCLOGALBANATE (allyl 2-(cyclohexyloxy)acetate); CYCLOHEXYL SALICYLATE (cyclohexyl 2-hydroxybenzoate); CYCLOMYRAL (8,8-dimethyl-1,2,3,4,5,6,7,8-octahydronaphthalene-2-carbaldehyde); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one); DAMASCONE DELTA 1-(2,6,6-trimethyl-1-cyclohex-3-enyl)but-2-en-1-one); DECENAL-4-TRANS ((E)-dec-4-ena 1); DELPHONE (2-pentylcyclopentanone); DIHYDRO ANETHOLE (1-methoxy-4-propylbenzene); DIHYDRO JASMONE (3-methyl-2-pentylcyclopent-2-enone); DIMETHYL BENZYL CARBINOL (2-methyl-1-phenylpropan-2-ol); DIMETHYL BENZYL CARBINYL ACETATE (2-methyl-1-phenylpropan-2-yl acetate); DIMETHYL BENZYL CARBINYL BUTYRATE (2-methyl-1-phenylpropan-2-yl butanoate); DIMETHYL OCTENONE (4,7-dimethyloct-6-en-3-one); DIMETOL (2,6-dimethylheptan-2-ol); DIPENTENE (1-methyl-4-(prop-1-en-2-yl) cyclohex-1-ene); DUPICAL ((E)-4-((3aS,7aS)-hexahydro-1H-4,7-methanoinden-5(6H)-ylidene)butanal); EBANOL ((E)-3-methyl-5-(2,2,3-trimethylcyclopent-3-en-1-yl)pent-4-en-2-ol); ETHYL CAPROATE (ethyl hexanoate); ETHYL CAPRYLATE (ethyl octanoate); ETHYL LINALOOL ((E)-3,7-dimethylnona-1,6-dien-3-ol); ETHYL LINALYL ACETATE ((Z)-3,7-dimethylnona-1,6-dien-3-yl acetate); ETHYL OENANTHATE (ethyl heptanoate); ETHYL SAFRANATE (ethyl 2,6,6-trimethylcyclohexa-1,3-diene-1-carboxylate); EUCALYPTOL ((1s,4s)-1,3,3-trimethyl-2-oxabicyclo[2.2.2]octane); FENCHYL ACETATE ((2S)-1,3,3-trimethylbicyclo[2.2.1]heptan-2-yl acetate); FENCHYL ALCOHOL ((1S,2R,4R)-1,3,3-trimethylbicyclo[2.2.1]heptan-2-ol); FIXOLIDE (1-(3,5,5,6,8,8-hexamethyl-5,6,7,8-tetrahydronaphthalen-2-yl)ethanone); FLORALOZONE (3-(4-ethylphenyl)-2,2-dimethylpropanal); FLORHYDRAL (3-(3-isopropylphenyl)butanal); FLOROCYCLENE ((3a R,6S,7aS)-3a,4,5,6,7,7a-hexahydro-1H-4,7-methanoinden-6-yl propionate); FLOROPAL (2,4,6-trimethyl-4-phenyl-1,3-dioxane); FRESKOMENTHE (2-(sec-butyl)cyclohexa none); FRUITATE ((3aS,4S,7R,7aS)-ethyl octahyd ro-1H-4,7-methanoindene-3a-carboxylate); FRUTONILE (2-methyldecanenitrile); GALBANONE PURE (1-(5,5-dimethylcyclohex-1-en-1-yl)pent-4-en-1-one); GARDOCYCLENE ((3aR,6S,7aS)-3a,4,5,6,7,7a-hexahydro-1H-4,7-methanoinden-6-yl 2-methylpropanoate); GERANIOL ((E)-3,7-dimethylocta-2,6-dien-1-ol); GERANYL ACETATE SYNTHETIC ((E)-3,7-dimethylocta-2,6-dien-1-yl acetate); GERANYL ISOBUTYRATE ((E)-3,7-dimethylocta-2,6-dien-1-yl 2-methylpropanoate); GIVESCONE (ethyl 2-ethyl-6,6-dimethylcyclohex-2-enecarboxylate); HABANOLIDE ((E)-oxacyclohexadec-12-en-2-one); HEDIONE (methyl 3-oxo-2-pentylcyclopentaneacetate); HERBANATE ((2S)-ethyl 3-isopropylbicyclo[2.2.1]hept-5-ene-2-carboxylate); HEXENYL-3-CIS BUTYRATE ((Z)-hex-3-en-1-yl butanoate); HEXYL CINNAMIC ALDEHYDE ((E)-2-benzylideneoctanal); HEXYL ISOBUTYRATE (hexyl 2-methyl-propanoate); HEXYL SALICYLATE (hexyl 2-hydroxybenzoate); INDOFLOR (4,4a,5,9b-tetrahydroindeno[1,2-d][1,3]dioxine); IONONE BETA ((E)-4-(2,6,6-trimethylcyclohex-1-en-1-yl)but-3-en-2-one); IRISONE ALPHA ((E)-4-(2,6,6-trimethylcyclohex-2-en-1-yl)but-3-en-2-one); IRONE ALPHA ((E)-4-(2,5,6,6-tetramethylcyclohex-2-en-1-yl)but-3-en-2-one); ISO E SUPER (1-(2,3,8,8-tetramethyl-1,2,3,4,5,6,7,8-octahydronaphthalen-2-yl)ethanone); ISOCYCLOCITRAL (2,4,6-trimethylcyclohex-3-enecarbaldehyde); ISONONYL ACETATE (3,5,5-trimethylhexyl acetate); ISOPROPYL METHYL-2-BUTYRATE (isopropyl 2-methyl butanoate); ISORALDEINE 70 ((E)-3-methyl-4-(2,6,6-trimethylcyclohex-2-en-1-yl)but-3-en-2-one); JASMACYCLENE ((3aR,6S,7aS)-3a,4,5,6,7,7a-hexahydro-1H-4,7-methanoinden-6-yl acetate); JASMONE CIS ((Z)-3-methyl-2-(pent-2-en-1-yl)cyclopent-2-enone); KARANAL (5-(sec-butyl)-2-(2,4-dimethylcyclohex-3-en-1-yl)-5-methyl-1,3-dioxane); KOAVONE ((Z)-3,4,5,6,6-pentamethylhept-3-en-2-one); LEAF ACETAL ((Z)-1-(1-ethoxyethoxy)hex-3-ene); LEMONILE ((2E,6Z)-3,7-dimethylnona-2,6-dienenitrile); LIFFAROME GIV ((Z)-hex-3-en-1-yl methyl carbonate); LILIAL (3-(4-(tert-butyl)phenyl)-2-methylpropanal); LINALOOL (3,7-dimethylocta-1,6-dien-3-ol); LINALYL ACETATE (3,7-dimethylocta-1,6-dien-3-yl acetate); MALTYL ISOBUTYRATE (2-methyl-4-oxo-4H-pyran-3-yl 2-methylpropanoate); MANZANATE (ethyl 2-methylpentanoate); MELONAL (2,6-dimethylhept-5-enal); MENTHOL (2-isopropyl-5-methylcyclohexanol); MENTHONE (2-isopropyl-5-methylcyclohexanone); METHYL CEDRYL KETONE (1-((1S,8aS)-1,4,4,6-tetramethyl-2,3,3a,4,5,8-hexahydro-1H-5,8a-methanoazulen-7-yl)ethanone); METHYL NONYL KETONE EXTRA (undecan-2-one); METHYL OCTYNE CARBONATE (methyl non-2-ynoate); METHYL PAMPLEMOUSSE (6,6-dimethoxy-2,5,5-trimethylhex-2-ene); MYRALDENE (4-(4-methylpent-3-en-1-yl)cyclohex-3-enecarbaldehyde); NECTARYL (2-(2-(4-methylcyclohex-3-en-1-yl)propyl)cyclopentanone); NEOBERGAMATE FORTE (2-methyl-6-methyleneoct-7-en-2-yl acetate); NEOFOLIONE ((E)-methyl non-2-enoate); NEROLIDYLE ((Z)-3,7,11-trimethyldodeca-1,6,10-trien-3-yl acetate); NERYL ACETATE HC ((Z)-3,7-dimethylocta-2,6-dien-1-yl acetate); NONADYL (6,8-dimethylnonan-2-ol); NONENAL-6-CIS ((Z)-non-6-enal); NYMPHEAL (3-(4-isobutyl-2-methylphenyl)propanal); ORIVONE (4-(tert-pentyl)cyclohexanone); PARADISAMIDE (2-ethyl-N-methyl-N-(m-tolyl)butanamide); PELARGENE (2-methyl-4-methylene-6-phenyltetrahydro-2H-pyran); PEONILE (2-cyclohexylidene-2-phenylacetonitrile); PETALIA (2-cyclohexylidene-2-(o-tolyl)acetonitrile); PIVAROSE (2,2-dimethyl-2-pheylethyl propanoate); PRE-CYCLEMONE B (1-methyl-4-(4-methylpent-3-en-1-yl)cyclohex-3-enecarbaldehyde); PYRALONE (6-(sec-butyl)quinoline); RADJANOL SUPER ((E)-2-ethyl-4-(2,2,3-trimethylcyclopent-3-en-1-yl)but-2-en-1-ol); RASPBERRY KETONE (N112) (4-(4-hydroxyphenyl)butan-2-one); RHUBAFURANE (2,2,5-trimethyl-5-pentylcyclopentanone); ROSACETOL (2,2,2-trichloro-1-phenylethyl acetate); ROSALVA (dec-9-en-1-ol); ROSYFOLIA ((1-methyl-2-(5-methyl hex-4-en-2-yl)cyclopropyl)-methanol); ROSYRANE SUPER (4-methyl-2-phenyl-3,6-dihydro-2H-pyran); SERENOLIDE (2-(1-(3,3-dimethylcyclohexyl)ethoxy)-2-methylpropyl cyclopropanecarboxylate); SILVIAL (2-methyl-3-[4-(2-methylpropyl)phenyl]propanal); SPIROGALBANONE (1-(spiro[4.5]dec-6-en-7-yl)pent-4-en-1-one); STEMONE ((E)-5-methylheptan-3-one oxime); SUPER MUGUET ((E)-6-ethyl-3-methyloct-6-en-1-ol); SYLKOLIDE ((E)-2-((3,5-dimethylhex-3-en-2-yl)oxy)-2-methylpropyl cyclopropanecarboxylate); TERPINENE GAMMA (1-methyl-4-propan-2-ylcyclohexa-1,4-diene); TERPINOLENE (1-methyl-4-(propan-2-ylidene)cyclohex-1-ene); TERPINYL ACETATE (2-(4-methylcyclohex-3-en-1-yl)propan-2-yl acetate); TETRAHYDRO LINALOOL (3,7-dimethyloctan-3-ol); TETRAHYDRO MYRCENOL (2,6-dimethyloctan-2-ol); THIBETOLIDE (oxacyclohexadecan-2-one); TRIDECENE-2-NITRILE ((E)-tridec-2-enenitrile); UNDECAVERTOL ((E)-4-methyldec-3-en-5-ol); VELOUTONE (2,2,5-trimethyl-5-pentylcyclopentanone); VIRIDINE ((2,2-dimethoxyethyl)benzene); ZINARINE (2-(2,4-dimethylcyclohexyl)pyridine); and mixture thereof.

The following non-limiting examples are intended to further illustrate the present invention.

Example 1 (Comparative Example)

Slurry of Aminoplast Microcapsules
Aminoplast microcapsules were obtained by using the following method:
1. A polymer stabilizer (ZeMac® E400, ex Vertellus) was dissolved in water under moderate shear mixing.
2. The temperature was adjusted to 35° C., the pH to 4.5 with sodium hydroxide, then an alkylolated triamine pre-condensate (Luracoll SD, ex BASF), urea and perfume composition were added.
3. The system was emulsified using a propeller operating at 1000 rpm.
4. The temperature was increased to 80° C. over a period of 3 h.
5. A second portion of the alkylolated triamine or triamine pre-condensate and formic acid were added, and then the reaction was left for 2 h at 80° C.
6. The system was cooled to room temperature.

The size of the microcapsules was measured by using the technique of laser diffraction, using a Mastersizer 2000 supplied by Malvern. The technique is based on the principle that the light from a coherent source, in this case the laser beam, will scatter as particles pass through the beam, with the angle of the scattered light being directly related to the size of the particles. A decrease in particle size results in a logarithmic increase in the observed scattering angle. The observed scattering intensity is also dependent on particle size and diminishes relative to the particle's cross-sectional area. Large particles therefore scatter light at narrow angles with high intensity, whereas small particles scatter at wider angles but with low intensity. Detectors are used to measure the scattered light pattern produced over a wide range of angles and, hence, determine the particle size distribution of the sample using an appropriate optical model.

For the measurement of the microcapsule size, the sample was placed in the Malvern Hydro2000 SM module, supplied with the Mastersizer 2000, for the measurement of wet dispersions. The supplied software was used to transform the measured scattered light pattern into the microcapsule size distribution. The optical model parameters used were 1.47 and 0 for the refractive index and absorption index, respectively. Sample measurement was taken over a period of five seconds using 5000 measurement snaps.

The volume-averaged microcapsule size obtained by this method was about 15 micrometers.

The zeta-potential of the microcapsules was measured using the following method:

The slurry obtained was filtered, and the microcapsules were washed 5 times with distilled water and re-dispersed again in distilled water. Then 2 g of this dispersion was added to 8 g of a potassium dihydrogen phosphate/sodium hydrogen phosphate buffer solution at pH 7 having an ion concentration of 7×110⁴ mol/l. The measurement was performed using a Zetasizer Nano Z, equipped with a laser with a wavelength of 633 nm. A value of −50 mV was obtained.

Example 2

Slurry of aminoplast microcapsules comprising post-added cationic polyampholyte (comparative example)

The steps 1-5 from Example 1 were repeated and the process was continued by performing the following steps:

6. To 90 g of obtained slurry, 10 g Merquat 281 solution (cationic polyampholyte commercially available as 35% solution), the pH of which had been adjusted beforehand to a value of 4.5 using sodium hydroxide, were added stepwise over 10 min. The slurry was maintained under agitation while the cationic polyampholyte was added at room temperature.

7. The modified slurry was left under agitation for 1 h.

Example 3

Slurry of aminoplast microcapsules, wherein the cationic polyampholyte is embedded in the shell of the microcapsules The steps 1-4 from Example 1 were repeated and the process was continued by performing the following steps:

5. A 1.25% of Merquat 281 solution, the pH of which had been adjusted to 4.5 with sodium hydroxide, was added stepwise over 10 min. The slurry was maintained under agitation for 30 min at 80° C.

6. A second portion of the alkylolatedtriamine or triamine pre-condensate and formic acid were added and then the reaction was left for 2 h at 80° C. The system was cooled to room temperature.

7. The modified slurry is left under agitation for 1 h.

Example 4

Slurry Stability and Aggregation in Liquid Detergent

The slurries obtained in Examples 1-3 were rated in terms of encapsulation efficiency: Slurry was rated as "++" if the amount of solid material (shell material+fragrance oil) was close to the theoretical value of 42% of the slurry, and "+" if the amount of solid was above 39%. The slurry was rated as unacceptable ("−") if the solid content was below 39%.

Satisfying slurries were then incorporated in two different commercial liquid detergent bases at a level of 0.5% of slurry by weight of the base. The samples were stored for 1 week at room temperature (RT), and flocculation was assessed via visual inspection.

TABLE 1

Formulation trials and scores (all % values are weight %)

| Entry | Example 1 comparative slurry | Example 2 comparative slurry | Example 3 Test Slurry | Slurry rating | Aggregation in liquid detergent A after 1 week at RT | Aggregation in liquid detergent B after 1 week at RT |
|---|---|---|---|---|---|---|
| 1 | no polyampholyte | — | — | ++ | Yes | Yes |
| 2 | — | 2% Merquat 281 | — | ++ | Yes | Yes |
| 3 | | 3% Merquat 281 | — | ++ | Yes | Yes |
| 4 | | 5% Merquat 281 | — | ++ | Yes | Yes |
| 6 | | — | 0.5% Merquat 281 | ++ | No | No |
| 7 | | 3% Merquat 3330 | — | ++ | Yes | Yes |
| 8 | | — | 0.5% Merquat 3330 | + | No | No |
| 9 | | 3% Merquat 100 | | ++ | Yes | Yes |
| 10 | | — | 0.5% Merquat 100 | + | Yes | Yes |

As apparent from Table 1, the addition of 3 wt % and more cationic polyampholyte to the slurry was not effective in preventing the microcapsules to aggregating in the liquid detergent. On the other hand, embedding as low as 0.5 wt % of cationic polyampholyte within the shell of the microcapsules was sufficient to provide the desired benefit. Finally, the lack of performance of Merquat 100, which has 100% cationic units in its constitution, confirms the necessity of the polyampholyte character of the polymer to provide the desired stabilization effect. The same results are obtained in detergents for pouches having different origins, confirming thereby the robustness of the stabilizing effect provided by the cationic polyampholyte according to the present invention.

Example 5

Olfactive Assesment:

Terry towels were washed in a EU washing machine at 40° C. with 75 g of standard commercial liquid detergent (detergent A in Example 4) comprising 0.5% of slurry by weight of base, according to entries 1, 2, 6 and 8 as described in Table 1. The olfactive performance was assessed by a panel of four experts on wet stage and after drying for 24 h at room temperature (pre-rub and post-rub), and it was rated on a scale of 1-5.

TABLE 2

| Entry | Post added cationic polyampholyte (Ex 2) | Embedded Cationic polyampholyte (Ex 3) | Wet | Pre-rub | Post-rub |
|---|---|---|---|---|---|
| 1 | — | — | 1 | 1 | 2 |
| 2 | 3% Merquat | — | 1 | 2 | 2.5 |
| 6 | — | 0.5% Merquat, 281 | 1 | 2.5 | 3.5 |
| 8 | — | 0.5% Merquat 3330 | 1 | 2 | 3 |

As apparent from Table 2, adding a cationic polyampholyte was beneficial to the sensory performance of the perfume on dry fabrics. The best results were obtained with samples having the polyampholyte embedded within the shell of the microcapsules.

The invention claimed is:

1. An encapsulated perfume composition comprising at least aminoplast core-shell microcapsule bearing a net-negative charge, wherein the said core-shell is dispersed in an aqueous dispersing medium, wherein the shell of said core-shell microcapsule has embedded in it a cationic polyampholyte.

2. An encapsulated perfume composition according to claim 1, wherein the cationic polyampholyte comprises 2 to 99 mol % of a cationic or cation-forming functional group; and 1 to 98 mol % of an anion-forming functional group; and 0 to 50 mol % of a non-ionic functional group.

3. An encapsulated perfume composition according to claim 1, wherein the cationic polyampholyte is a copolymer of from 2 to 99 mol % of dimethyldiallyl ammonium chloride (DADMAC); and 1 to 98 mol % of acrylic acid or methacrylic acid; and 0 to 50 mol % of acrylamide.

4. An encapsulated perfume composition according to claim 3, wherein the cationic polyampholyte is a copolymer of from 30 to 95 mol % of dimethyldiallyl ammonium chloride (DADMAC).

5. An encapsulated perfume composition according to claim 4, wherein the cationic polyampholyte is a copolymer of from 60 to 90 mol % of dimethyldiallyl ammonium chloride (DADMAC).

6. An encapsulated perfume composition according to claim 3, wherein the cationic polyampholyte is a copolymer of from 5 to 70 mol % of acrylic acid or methacrylic acid.

7. An encapsulated perfume composition according to claim 6, wherein the cationic polyampholyte is a copolymer of from 10 to 40 mol % of acrylic acid or methacrylic acid.

8. An encapsulated perfume composition according to claim 3, wherein the cationic polyampholyte is a copolymer of from 0.1 to 5 mol % of acrylamide.

9. An encapsulated perfume composition according to claim 1, wherein the cationic polyampholyte is a copolymer of 2 to 99 mol % of methacrylamidopropyl-trimethylammonium chloride (MAPTAC); and 1 to 98 mol % of acrylic acid or methacrylic acid; and 0 to 50 mol % of acrylamide.

10. An encapsulated perfume composition according to claim 9, wherein the cationic polyampholyte is a copolymer of 30 to 95 mol % of methacrylamidopropyl-trimethylammonium chloride (MAPTAC).

11. An encapsulated perfume composition according to claim 10, wherein the cationic polyampholyte is a copolymer of 60 to 90 mol % of methacrylamidopropyl-trimethylammonium chloride (MAPTAC).

12. An encapsulated perfume composition according to claim 9, wherein the cationic polyampholyte is a copolymer of 5 to 70 mol % of acrylic acid or methacrylic acid.

13. An encapsulated perfume composition according to claim 12, wherein the cationic polyampholyte is a copolymer of 10 to 40 mol % of acrylic acid or methacrylic acid.

14. An encapsulated perfume composition according to claim 9, wherein the cationic polyampholyte is a copolymer of 0.1 to 5 mol % of acrylamide.

15. A non-suspending liquid detergent composition comprising an anionic surfactant and an encapsulated perfume composition as defined in claim 1.

16. A detergent composition according to claim 15, containing less than 20 wt % of water, enclosed within a water soluble or water-dispersible pouch.

17. A detergent composition according to claim 15, having a pH of 10 or lower.

18. A method of forming the encapsulated perfume composition as defined in claim 1, said method comprising the steps of:
   I) encapsulating at least one perfume-containing droplet in a shell comprising a cross-linked aminoplast resin to form a slurry comprising a dispersion of at least one aminoplast core-shell microcapsule bearing a net negative charge; and
   II) adding to the slurry, simultaneously or sequentially, a cationic polyampholyte, an amino-aldehyde pre-condensate, and a cross-linker, under conditions whereby the pre-condensate and cross-linker react to form a matrix cross-linked aminoplast resin around the core-shell microcapsule, in which matrix the cationic polyampholyte is embedded.

19. A method according to claim 18, comprising the steps of:
   I) mixing together, at a temperature of 35° C. and a pH of 4.5, a polymeric stabilizer, perfume-containing oil, amino-aldehyde pre-condensate, and a cross-linker, in water and under moderate shear;
   II) emulsifying the mixture to obtain a desired average droplet size range and droplet size distribution;
   III) raising the temperature above 80° C. over a period of 3 h to form a cross-linked aminoplast resin shell around the droplets, thereby forming a slurry of core-shell microcapsules;
   IV) at a pH of 4.5, adding sequentially or simultaneously the cationic polyampholyte, amino-aldehyde pre-condensate and a cross-linker, and keeping the temperature above 80° C. over a period of 2 h, forming a matrix of cross-linked aminoplast resin around the core-shell microcapsules, in which matrix the cationic polyampholyte is embedded; and
   V) cooling the resultant slurry.

20. A method according to claim 19, wherein in step IV) the cationic polyampholyte is first added to the slurry, before the subsequent addition of amino-aldehyde pre-condensate and cross-linker.

* * * * *